United States Patent [19]

Paetz et al.

[11] Patent Number: 4,670,608

[45] Date of Patent: Jun. 2, 1987

[54] PREPARATION OF 2,4-DICHLORO-3-ALKYL-6-NITRO-PHENOLS

[75] Inventors: Christian Paetz, Bergisch Gladbach; Karlfried Wedemeyer, Cologne, both of Fed. Rep. of Germany

[73] Assignee: Bayer Aktiengesellschaft, Leverkusen, Fed. Rep. of Germany

[21] Appl. No.: 826,710

[22] Filed: Mar. 19, 1986

Related U.S. Application Data

[63] Continuation of Ser. No. 764,891, Aug. 12, 1985, abandoned.

[51] Int. Cl.$^4$ .............................................. C07C 79/32
[52] U.S. Cl. ................................................... 568/709
[58] Field of Search ......................................... 568/709

[56] References Cited

U.S. PATENT DOCUMENTS

| | | | |
|---|---|---|---|
| 3,363,010 | 1/1968 | Schwertzenbek | 568/779 |
| 3,413,341 | 11/1968 | Bursack | 568/778 |
| 3,772,002 | 11/1973 | Ramello | 96/100 |
| 3,903,178 | 9/1975 | Nakumura et al. | 568/709 |
| 3,928,470 | 12/1975 | Soula | 568/709 |
| 4,038,328 | 7/1977 | Pelster | 568/709 |
| 4,310,711 | 1/1982 | Müller et al. | 568/709 |
| 4,489,210 | 12/1984 | Judat et al. | 568/779 |

FOREIGN PATENT DOCUMENTS

| | | | |
|---|---|---|---|
| 2216804 | 4/1972 | Fed. Rep. of Germany | 568/709 |
| 2614264 | 6/1977 | Fed. Rep. of Germany | 568/709 |
| 2297836 | 8/1976 | France | 568/709 |

OTHER PUBLICATIONS

Chemical Abstracts, vol. 95, No. 9, 8/31/81, p. 728, No. 80326k.
Chemical Abstracts, vol. 82, No. 13, 3/31/75, p. 504, No. 86163h.

Primary Examiner—Werren B. Lone
Attorney, Agent, or Firm—Sprung, Horn, Kramer & Woods

[57] ABSTRACT 2,4-Dichloro-3-alkyl-6-nitrophenols are prepared by chlorinating, with chlorine in the presence of a catalyst, 1-alkyl-4-nitrobenzenes having a $C_2$–$C_8$-alkyl radical until the content of trichloroalkylnitrobenzenes is at least 60% by weight in the chlorination mixture, removing the catalyst from the chlorination mixture, then hydrolyzing the chlorination mixture, removing the precipitated reaction product, and treating it with an aqueous inorganic acid. The 2,4-dichloro-3-alkyl-6-nitrophenols are new.

10 Claims, No Drawings

PREPARATION OF 2,4-DICHLORO-3-ALKYL-6-NITROPHENOLS

This is a continuation of application Ser. No. 764,891, filed Aug. 12, 1985, abandoned.

The invention relates to new 2,4-dichloro-3-alkyl-6-nitrophenols and to a process for their preparation.

The preparation of 2,4-dichloro-3-methyl-6-nitrophenol starting from 4-chloro-5-methylphenol, by initially sulphonating the latter, then chlorinating and subsequently nitrating, has been disclosed (see, for example, German Auslegeschrift No. 2,501,899, German Offenlegungsschrift No. 2,216,804, British Patent Specification No. 1,361,714 and Japanese Pat. No. 72 34 326).

The disadvantages of this process are, on the one hand, the large number of reaction stages which have to be passed through and, on the other hand, the difficulty of obtaining the required starting materials. It is known that m-alkylphenols, for example m-cresol, and the 4-chloro-5-alkylphenols prepared from them can be prepared pure only with great difficulty. Thus, for example for the preparation of m-ethylphenol German Offenlegungsschrift No. 2,229,776 describes the diazotization and boiling of m-aminoacetophenone which has been prepared by nitration of acetophenone followed by reduction. A process for the preparation of m-alkylphenols is described, in European Patent Specification No. 80,880, in which initially alkylbenzenes are sulphonated to give a mixture of o-, m- and p-isomers, then the o- and p-alkylbenzenesulphonic acids which have been formed are desulphonated, and subsequently the remaining m-alkylbenzenesulphonic acid is subjected to fusion with an alkali. Another possibility for the preparation of m-alkylphenol comprises the isomerization of the o-alkylphenol, which is relatively easy to obtain, on a catalyst (Houben-Weyl, Methoden der organischen Chemie (Methods of Organic Chemistry), Vol. VI/1c, pages 1073–1081). A mixture of the o-, m- and p-isomers of alkylphenols is thereby produced. The disadvantages of this process is that not only isomerization but also transalkylation takes place, that is to say the formation of phenol and more highly alkylated phenols, and this process can be applied only for alkyl groups which themselves form stable carbocations. An additional disadvantage is that, in the necessary work-up of the mixture of isomers by distillation, the m-alkylphenol fraction can only be removed as a mixture of the m- and p-isomers because the difference in boiling points is too small. In order to remove the m-alkylphenol from the mixture of m- and p-isomers, selective chlorination with relatively costly sulphuryl chloride is necessary, the m-alkylphenol being chlorinated to give 4-chloro-5-alkylphenol which is now readily amenable to separation by distillation. However, the disadvantage of this separation process is that not only the desired 4-chloro-5-alkylphenol but also the corresponding o-chlorophenols appear, and these can amount to up to 40% by weight of the yield.

A process for the preparation of 2,4-dichloro-3-alkyl-6-nitrophenols of the general formula (I)

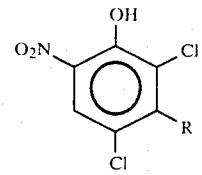

in which
R represents an alkyl radical having 2 to 8 carbon atoms, has now been found, which is characterized in that 1-alkyl-4-nitrobenzenes of the general formula (II)

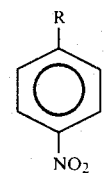

in which
R has the abovementioned meaning,
are chlorinated, with chlorine in the presence of a catalyst, up to a content of trichloroalkylnitrobenzene of at least 60% by weight in the chlorination mixture, the catalyst is removed from the chlorination mixture, then the chlorination mixture is hydrolyzed, and the precipitated reaction product is removed and treated with an aqueous inorganic acid.

The 2,4-dichloro-3-alkyl-6-nitrophenols of the general formula (I)

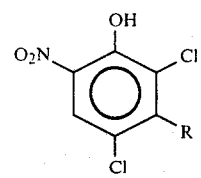

in which
R represents an alkyl radical having 2 to 8 carbon atoms,
which are prepared by the process according to the invention are new.

The 1-alkyl-4-nitrobenzenes used in the process according to the invention preferably have a $C_2$–$C_6$-, particularly preferably a $C_2$–$C_4$-, alkyl radical.

Examples of alkyl radicals which may be mentioned are the ethyl, the propyl, the butyl, the pentyl, the hexyl, the cyclohexyl, the heptyl and the octyl radical, preferably the ethyl, the propyl and the butyl radical.

New 2,4-dichloro-3-alkyl-6-nitrophenols which can be prepared by the process according to the invention and which may be mentioned are: 2,4-dichloro-3-ethyl-6-nitrophenol, 2,4-dichloro-3-isopropyl-6-nitrophenol, 2,4-dichloro-3-tert.-butyl-6-nitrophenol, 2,4-dichloro-3-cyclohexyl-6-nitrophenol and 2,4-dichloro-3-isoamyl-6-nitrophenol, preferably 2,4-dichloro-3-ethyl-6-nitrophenol, 2,4-dichloro-3-isopropyl-6-nitrophenol and 2,4-dichloro-3-tert.-butyl-6-nitrophenol.

The catalysts which can be used in the process according to the invention are all known chlorination catalysts as are described in, for example, Houben-Weyl, Vol. V/3, pages 651–725. Examples which may be mentioned are: iron(III), chloride, antimony(III) chloride, aluminum(III) chloride and iodine. The chlorination catalysts can be used in the process according to the invention either alone or mixed together.

The amount of the chlorination catalyst is not critical for the process according to the invention, and it can be readily determined by preliminary experiments. The amount of catalyst usually used in the process according to the invention is about 1 to 10, preferably, 4 to 7, % by weight relative to the 1-alkyl-4-nitrobenzene used.

For the chlorination of the 1-alkyl-4-nitrobenzenes, the latter can be used either as the pure substance or dissolved in an inert organic solvent. Suitable and preferred inert organic solvents are halogenated aliphatic hydrocarbons, such as methylene chloride, chloroform and/or tetrachloroethane. However, it is also possible to use other inert organic solvents, such as nitrobenzene, o-chloronitrobenzene, 1,2,4-trichlorobenzene and/or $CS_2$ (see Houben-Weyl, Vol. V/3, page 674).

The amount of the inert organic solvent to be used is not critical for the process according to the invention, and it can be varied within wide limits. It is merely necessary for an amount sufficient to dissolve the 1-alkyl-4-nitrobenzene to be present. The inert organic solvents are usually used in an amount of about 1 to 10 liters, preferably 2 to 4 liters, per kg of 1-alkyl-4-nitrobenzene to be used.

The chlorination of the 1-alkyl-4-nitrobenzenes can be carried out at temperatures from about 0° to 150° C., preferably at 30° to 80° C.

In the process according to the invention, the chlorination of the 1-alkyl-4-nitrobenzenes is continued up to a content of 1,3,4-trichloro-2-alkyl-5-nitrobenzene of at least 60% by weight, preferably 70 to 90% by weight, particularly preferably 75 to 85% by weight, in the chlorination mixture. This entails the molar ratio of chlorine to 1-alkyl-4-nitrobenzene being about 2:1 to 4:1, preferably 2.7:1 to 3.5:1.

The chlorination catalyst used is removed from the chlorination product resulting from the chlorination by employing customary processes, such as washing with water (see, for example, Houben-Weyl, Vol. V/3, pages 651-725), and the product is then used for the hydrolysis.

The hydrolysis mixture used for the hydrolysis of the resulting chlorination product consists of water and an organic solvent which is miscible with water, and contains a compound with an alkaline reaction. Lower alcohols, ketones and/or cyclic ethers can be used as the organic solvents which are miscible with water. However, $C_1$-$C_5$-alcohols are preferably used, such as methanol, ethanol, propanol, isopropanol, butanol and/or isobutanol, particularly preferably methanol. The amount of the solvent mixture used in the hydrolysis is not critical and can be varied. It is merely necessary to use an amount sufficient to ensure the stirrability of the hydrolysis mixture.

The compounds having an alkaline reaction which can be used are alkali metal and/or alkaline earth metal hydroxides, oxides, carbonates and/or acetates. However, the alkali metal hydroxides are preferably used in the process according to the invention.

The ratio of the amounts of the reactants used in the hydrolysis, that is to say the compound having an alkaline reaction and the chlorinated product, can be varied within wide limits. The most favorable amount can readily be determined by preliminary experiments. About 2 to 10, preferably 5 to 7, moles of compound having an alkaline reaction are usually used per mole of hydrolyzable chlorine.

The temperature of the hydrolysis reaction can likewise vary within wide limits, and the lower limit is determined by the hydrolysis reaction rate and the upper limit is determined by operating at the particular boiling point of the hydrolysis mixture under atmospheric pressure. The hydrolysis is preferably carried out at temperatures from about 20° to 100° C., particularly preferably at 40° to 80° C.

After the hydrolysis is complete, the reaction product which precipitates out, where appropriate on cooling the hydrolysis mixture, is filtered off with suction, and the appropriate alkali metal or alkaline earth metal salt of the 2,4-dichloro-3-alkyl-6-nitrophenol is obtained in the virtually pure form. On the other hand, all the by-products formed or carried over from the chlorination stage and the hydrolysis stage remain in the filtrate.

To prepare the free phenols, the resulting nitrophenolate is treated with an aqueous inorganic acid, such as aqueous hydrochloric acid and/or aqueous sulphuric acid, by known processes (see, for example, Houben-Weyl, Volume VI/1c, pages 146-173).

The process according to the invention can be represented by the equation below:

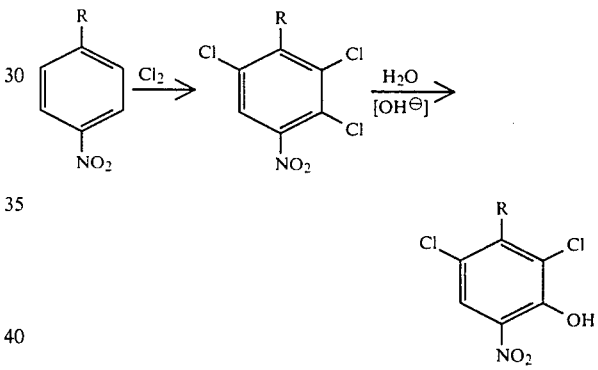

The process according to the invention can be carried out both continuously and discontinuously.

The 2,4-dichloro-3-alkyl-6-nitrophenols prepared by the process according to the invention are produced in high purity and with high yields.

Compared with the known processes (for example German Offenlegungsschrift No. 2,216,804 and German Offenlegungsshcrift No. 2,501,829), which prepare 2,4-dichloro-3-methyl-6-nitrophenol starting from m-methylphenol, the number of reaction stages is greatly reduced in the process according to the invention, which contributes to the economic efficiency of the process according to the invention. In addition, the process according to the invention lacks labor-intensive separation processes, such as precision vacuum distillations. Furthermore, the procedure proposed within the scope of the invention can be carried out without the use of special apparatus as is necessary, for example, for the isomerization of alkylphenols to give a mixture of the o-, m- and p-alkylphenol isomers, because of the very high temperatures.

It is particularly surprising in the process according to the invention that the chlorination of 1-alkyl-4-nitrobenzene with chlorine leads to a particularly high content of 1,3,4-trichloro-2-alkyl-5-nitrobenzenes in the chlorination mixture (about 75 to 85% of 1,3,4-trichloro-2-alkyl-5-nitrobenzene in addition to 5 to 10% of dichloro-1-alkyl-4-nitrobenzene and 5 to 20% of tetrachloro-1-alkyl-4-nitrobenzene). It is also surprising that the hydrolysis of the 1,3,4-trichloro-2-alkyl-5-nitrobenzene having a $C_2$-$C_8$-alkyl radical leads selectively to the 2,4-dichloro-3-alkyl-6-nitrophenol, since in the hydrolysis of 1,3,4-trichloro-2-methyl-5-nitrobenzene it is not the corresponding 2,4-dichloro-3-methyl-6-nitrophenol which is formed but, by dehydrogenation, a 10-fold substituted diphenyl (2,2'-dinitro-3,3',4,4',6,6'-hexachloro-5,5'-dimethylbiphenyl).

The new 2,4-dichloro-3-alkyl-6-nitrophenols obtained by the process according to the invention can be converted into the corresponding amino compounds by reduction in a known manner, and these are used as intermediates for the preparation of cyan couplers for photographic papers (see, for example, German Offenlegungsschrift No. 2,028,601).

For example, the reduction of the 2,4-dichloro-3-alkyl-6-nitrophenols of the formula (I) to the corresponding 2,4-dichloro-3-alkyl-6-aminophenols of the formula (III)

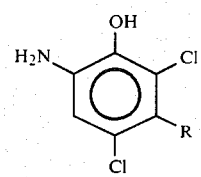
(III)

in which
R represents an alkyl radical having 2 to 8 carbon atoms,
can be carried out catalytically, for example using a palladium/active charcoal catalyst, or using a Raney nickel catalyst, or by reduction with iron in glacial acetic acid.

The 2,4-dichloro-3-alkyl-6-aminophenols and their hydrochlorides of the formula (III) are likewise new. The following new compounds may be mentioned as examples: 2,4-dichloro-3-ethyl-6-aminophenol, 2,4-dichloro-3-isopropyl-6-aminophenol, 2,4-dichloro-3-tert.-butyl-6-aminophenol and 2,4-dichloro-3-cyclohexyl-6-aminophenol and 2,4-dichloro-3-isoamyl-6-aminophenol, preferably 2,4-dichloro-3-ethyl-6-aminophenol, 2,4-dichloro-3-isopropyl-6-aminophenol and 2,4-dichloro-3-tert.-butyl-6-aminophenol.

The examples which follow are intended to illustrate the process according to the invention but without restricting it to the examples.

EXAMPLE 1

906 g (6 moles) of 1-ethyl-4-nitrobenzene were reacted with chlorine, with the addition of 18 g of Fe and 0.5 g of $I_2$, at 35° C. until the proportion of 1,3,4-trichloro-2-ethyl-5-nitrobenzene in the crude product amounted to 82-85%; about 3.2 moles of chlorine per mole of starting material were necessary for this. The reaction product was washed with water/HCl or water until neutral and free of iron. In this way, 1,465 g of crude product of the following composition were obtained:

| | |
|---|---|
| 5.8% } | isomeric dichloroethylnitrobenzenes |
| 1.9% | |
| 83.6% | trichloroethylnitrobenzene |
| 6.4% | tetrachloroethylnitrobenzene. |

EXAMPLE 2

495 g (3 moles) of 4-nitrocumene were chlorinated with elementary chlorine, with the addition of 8 g of $SbCl_3$ and 0.5 g of $I_2$, at 38° C. until the proportion of 2,3,6-trichloro-4-nitrocumene amounted to 76% in the crude product, about 3.65 moles of chlorine per mole of starting material being necessary for this. The reaction product was washed with concentrated HCl or, subsequently, with water until neutral and free of catalyst. In this way, 817.3 g of crude product of the following composition were obtained:

| | |
|---|---|
| 5.2% } | isomeric dichloronitrocumenes |
| 0.8% | |
| 75.3% | 2,3,6-trichloro-4-nitrocumene |
| 18.7% | tetrachloronitrocumene. |

EXAMPLE 3

18 g of Fe and 1 g of $I_2$ were added to a solution of 906 g (6 moles) of 1-ethyl-4-nitrobenzene in 2,000 ml of tetrachloroethane, and then the introduction of chlorine was started at 40° C. The chlorination was terminated after the composition of the crude product corresponded to that in Example 1, and it was washed until neutral and free of iron by addition of water/HCl or water. After removal of the solvent by distillation, if necessary in vacuo, 1,462 g of crude product of the composition indicated in Example 1 were obtained.

EXAMPLE 4

A mixture of 900 ml of methanol, 100 ml of $H_2O$ and 134 g of KOH was initially introduced into a round-bottomed flask, then heated to reflux temperature (73° C.) and, while stirring, 101.8 g of crude product from Example 1 were run in very rapidly. After refluxing for 4 hours, the solution had become dark red, and a red precipitate, the potassium salt of the nitrophenol which had been produced, had separated out. The mixture was cooled to room temperature, and the potassium nitrophenolate was filtered off with suction, washed first with 2×50 ml of methanol and then with 75 ml of cold water, and then the red solid, which was moist with water, was transferred into a second round-bottomed flask and stirred therein with 200 ml of 20% strength sulphuric acid at 70°-75° C. After about 3 hours, the free phenol had formed from the potassium nitrophenolate and had collected as a melt (melting point about 45° C.) on the bottom of the flask and could be removed by layer separation.

| Elemental analysis: | calculated | found |
|---|---|---|
| C | 40.7% | 40.7% |
| H | 2.9% | 2.9% |
| N | 5.9% | 5.9% |
| Cl | 30.1% | 30.2% |

Melting point: 45° C.
Yield: 61.8 g=79% based on the amount of trichloroethylnitrobenzene used; purity 97-98%.

EXAMPLE 5

A mixture of 900 ml of methanol, 100 ml of H$_2$O and 80 g of NaOH was initially introduced into a round-bottomed flask, then heated to reflux temperature and, with stirring, 103.5 g of 1,3,4-trichloro-2-ethyl-5-nitrobenzene, distilled material from the crude product from Example 1, was very rapidly run in as a melt (38° C.). After refluxing for 4 hours, the solution was dark red in color, and starting material was no longer detectable. The reaction mixture was cooled to room temperature, 2,000 ml of H$_2$O were added, and the mixture was acidified to pH 1 with 50% strength sulphuric acid and then extracted with 3×200 ml of chloroform. After evaporation of the solvent followed by steam distillation, 59.4 g of 2,4-dichloro-3-ethyl-6-nitrophenol were obtained, =63% of theory as 96% pure material.

EXAMPLE 6

When the amount of methanol in Example 5 was replaced by ethanol, the yield of desired final product was 53%.

EXAMPLE 7

When the amount of NaOH in Example 5 was replaced by an equivalent amount of potash or sodium acetate, again hydrolysis to give 2,4-dichloro-3-ethyl-6-nitrophenol took place; however, in these instances a considerably longer reaction time was necessary to achieve complete conversion.

EXAMPLE 8

When the amount of methanol in Example 5 was replaced by the same volume of acetone, a yield of 24% of 2,4-dichloro-3-ethyl-6-nitrophenol was obtained after a reaction time of 4 hours in the boiling solvent mixture.

EXAMPLE 9

53.7 g of crude chlorination product from Example 2, with a composition of 6% dichloronitrocumene, 75.3% 2,3,6-trichloro-3-nitrocumene and 18.7% tetrachloronitrocumene, were rapidly added, with stirring, to a boiling solution of 450 ml of methanol, 50 ml of H$_2$O and 67 g of KOH. After refluxing for 4 hours, a dark-red suspension had formed, and this was then cooled to room temperature and subsequently filtered off with suction. The solid which had been filtered off with suction was washed with 100 ml of methanolic potassium hydroxide solution, and then vigorously stirred with 120 ml of 20% strength H$_2$SO$_4$ and 300 ml of chloroform. After removal of the aqueous phase and evaporation of the solvent, 11.4 g of 2,4-dichloro-3-isopropyl-6-nitrophenol, of purity 97–98%, were obtained; the filtrate from the solid which had been filtered off with suction still contained 13.6 g of product, so that the total yield obtained was 65.4% of theory.

| Elemental analysis: | calculated | found |
| --- | --- | --- |
| C | 43.2% | 43.4% |
| H | 3.6% | 3.6% |
| N | 5.5% | 5.2% |
| Cl | 28.4% | 28.4% |

Melting point: 33° C.

EXAMPLE 10

Hydrogenation to give 2,4-dichloro-3-ethyl-6-aminophenol hydrochloride 34.4 g of 2,4-dichloro-3-ethyl-6-nitrophenol were hydrogenated in 180 ml of methanol in an autoclave, with the addition of 3 g of Raney Ni, at room temperature and under 10 bar of H$_2$. When hydrogen was no longer being absorbed, the pressure was released and, after addition of 0.4 ml of hydrazine hydrate, the catalyst was removed by filtration under protective gas and washed with 20 ml of methanol. 200 ml of concentrated HCl were added to the filtrate, cooling at 20° C., and thus the amine was precipitated as the hydrochloride. Filtration with suction under protective gas was again carried out, and the hydrochloride was washed with about 200 ml of cold acetone and dried in vacuo.

Yield 27.3 g of amine. HCl, material filtered with suction, purity ≧99% (HPLC), =82% of theory.

| Elemental analysis: | calculated | found |
| --- | --- | --- |
| C | 39.6% | 39.4% |
| H | 4.1% | 4.5% |
| N | 5.7% | 5.8% |
| Cl | 43.9% | 43.1% |

Melting point: 180° C. decomposition.

EXAMPLE 11

2,4-Dichloro-3-isopropyl-6-aminophenol hydrochloride 80 g (0.31 mole) of 2,4-dichloro-3-isopropyl-6-nitrophenol were hydrogenated in 425 ml of methanol with 5 g of Raney Ni in an autoclave at 25° to 30° C. and under 10 bar of H$_2$. The mixture was stirred for an additional 30 minutes after hydrogen was no longer being absorbed, then the pressure was released and, after addition of 0.5 ml of hydrazine hydrate to the hydrogenation solution, the catalyst was filtered off under protective gas, washed with 50 ml of methanol, and the filtrate was acidified with 200 ml of concentrated HCl, while cooling to 15° to 20° C. The precipitated crystals were filtered off with suction, washed with 200 ml of cold acetone and dried. Crystals I obtained comprised 53.5 g of 98% pure material; this is 70% of theory. A further 11–12 g of 85 to 90% pure material was obtained by evaporation of the wash acetone, this corresponding to 15% of theory. The hydrogenation mother liquor was discarded.

| Elemental analysis: | calculated | found |
| --- | --- | --- |
| C | 42.1% | 42.3% |
| H | 4.7% | 4.8% |
| N | 5.4% | 5.4% |
| Cl | 41.5% | 41.4% |

Melting point: 220° C. decomposition.

EXAMPLE 12

2,4-Dichloro-3-t.-butyl-6-aminophenol hydrochloride 64.8 g (0.24 mole) of 2,4-dichloro-3-t.-butyl-6-nitrophenol were hydrogenated in 400 ml of methanol with 5 g of Raney Ni in an autoclave at room temperature and under 10 bar of H$_2$. The mixture was stirred for an additional 30 minutes after hydrogen was no longer being absorbed, then the pressure was released and, after addition of 0.5 ml of hydrazine hydrate, the catalyst was filtered off under protective gas, washed with 50 ml of methanol, and then 200 ml of concentrated hydrochloric acid was added to the hydrogenation mother liquor while cooling to 20° C. The precipitated crystals were filtered off with suction, washed with 200 ml of cold acetone and dried.

Yield: Crystals I: 52.2 g as 96% pure material = 80% of theory.

| Elemental analysis: | calculated | found |
|---|---|---|
| C | 44.4% | 44.8% |
| H | 5.1% | 5.1% |
| N | 5.1% | 5.15% |
| Cl | 39.3% | 39.2% |

Melting point: 205° C. decomposition.

It will be understood that the specification and examples are illustrative but not limitative of the present invention and that other embodiments within the spirit and scope of the invention will suggest themselves to those skilled in the art.

We claim:

1. A process for the preparation of a 2,4-dichloro-3-alkyl-6-nitrophenol of the formula

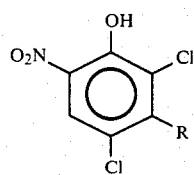

in which

R is an alkyl radical having 2 to 8 carbon atoms, which comprises chlorinating a 1-alkyl-4-nitrobenzene of the formula

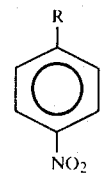

with chlorine at a temperature from 0° to 150° C. in the presence of iron (III) chloride, antimony(III) chloride, aluminum(III) chloride and or iodine as a catalyst, up to a content of trichloroalkylnitrobezene of at least 60% by weight in the chlorination mixture, removing the catalyst from the chlorination mixture, hydrolyzing the chlorination mixture with a hydrolysis mixture which comprises water, an organic solvent which is miscible with water, and a compound having an alkaline reaction thereby to form a precipitate, removing the precipitate and treating it with an aqueous inorganic acid.

2. A process according to claim 1, wherein the catalyst is used in 1 to 10% by weight relative to the 1-alkyl-4-nitrobenzene.

3. A process according to claim 1, wherein the chlorination of the 1-alkyl-4-nitrobenzenes is carried out up to a content of 70 to 90% by weight of 1,3,4-trichloro-2-alkyl-5-nitrobenzene in the chlorination mixture.

4. A process according to claim 1, wherein the molar ratio of chlorine to 1-alkyl-4-nitrobenzene is 2:1 to 4:1.

5. A process according to claim 1, wherein the compound having an alkaline reaction is present in 2 to 10 moles per mole of hydrolyzable chlorine.

6. A process according to claim 1, wherein the hydrolysis is carried out at a temperature from 20° to 100° C.

7. A process according to claim 1, wherein the organic solvent of the hydrolysis mixture is methanol.

8. A process according to claim 1, wherein the temperature during chlorination is from 30° to 80° C.

9. A process according to claim 1, wherein the temperature during hydrolysis is from 40° to 80° C.

10. A process according to claim 7, wherein the temperature during chlorination is from 30° to 80° C., the catalyst is used in 1 to 10% by weight relative to the 1-alkyl-4-nitrobenzene, the molar ratio of chlorine to 1-alkyl-4-nitrobenzene is 2:1 to 4:1, the chlorination of the 1-alkyl-4-nitrobenzenes is carried out up to a content of 70 to 90% by weight of 1,3,4-trichloro-2-alkyl-5-nitrobenzene in the chlorination mixture, the temperature during hydrolysis is from 40° to 80° C. and the compound having an alkaline reaction is present in 2 to 10 moles per mole of hydrolyzable chlorine.

* * * * *

UNITED STATES PATENT AND TRADEMARK OFFICE
CERTIFICATE OF CORRECTION

PATENT NO. : 4,670,608

DATED : June 2, 1987

INVENTOR(S) : Christian Paetz, et al.

It is certified that error appears in the above-identified patent and that said Letters Patent is hereby corrected as shown below:

Title Page      Before "Related U.S. Application Data" insert --[30] FOREIGN APPLICATION PRIORITY DATA August 29, 1984   Fed. Republic of Germany....3431687 --.

Title Page, under "U.S. Patent Documents"      line 4 - Delete "Nakumura" and substitute --Nakamura--
line 1 - Delete "Schwertzenbek" and substitute --Schwarzenbek--

Col. 6, line 67 and Col. 7, line 18      Delete " = " and substitute -- $\triangleq$ --

Signed and Sealed this

Eighth Day of December, 1987

Attest:

DONALD J. QUIGG

Attesting Officer      *Commissioner of Patents and Trademarks*